United States Patent [19]

Dieken et al.

[11] Patent Number: 4,706,674
[45] Date of Patent: Nov. 17, 1987

[54] ELECTRICAL STIMULATOR FOR BIOLOGICAL TISSUE UTILIZING OUTPUT CURRENT MONITOR

[75] Inventors: Alan P. Dieken, St. Paul; Joel R. Dufresne, Vadnais Heights, both of Minn.

[73] Assignee: Minnesota Mining and Manufacturing Co., St. Paul, Minn.

[21] Appl. No.: 744,977

[22] Filed: Jun. 17, 1985

[51] Int. Cl.⁴ ............................................. A61N 1/36
[52] U.S. Cl. ............................... 128/419 R; 128/421; 128/908
[58] Field of Search ................... 128/419 R, 421–423, 128/908

[56] References Cited

U.S. PATENT DOCUMENTS

| 321839A1 | 6/1983 | DEX. | |
| 4,068,669 | 1/1978 | Niemi | 128/419 R |
| 4,088,141 | 5/1978 | Niemi | 128/421 |
| 4,237,899 | 12/1980 | Hagfors et al. | 128/422 |
| 4,256,116 | 3/1981 | Meretsky et al. | 128/421 |
| 4,431,000 | 2/1984 | Butler et al. | 128/421 |
| 4,476,869 | 10/1984 | Bihn | 128/419 PT |

OTHER PUBLICATIONS

Buckett et al, "A Flexible Portable Functional Electrical Stimulation System, *36th ACEMB*, Sep. 12-14, 1983, p. 39.

Hogan, "Neuromuscular Stimulator Permits Customized Therapy", *Design News*, pp. 108-110, Sep. 17, 1984.

Hogan, "TENS Unit Modulates Output to Evade Body's Adaptive Capability", *Design News*, Sep. 17, 1984, pp. 114-115.

*Primary Examiner*—William E. Kamm
*Attorney, Agent, or Firm*—Donald M. Sell; James A. Smith; William D. Bauer

[57] ABSTRACT

An electrical stimulator for biological tissue utilizing an output current monitor. A drive circuit supplies a transformer output stage with the secondary winding of the transformer coupled across the electrode adapted to be connected to biological tissue. A current monitor and a reference impedance, being substantially greater than the load impedance, are coupled in series with each other and in parallel with the secondary winding and the electrode. In one embodiment, an additional current monitor is coupled in conjunction with the primary winding of the transformer and a comparator is used to compare currents measured by both current monitors.

6 Claims, 3 Drawing Figures

ELECTRICAL STIMULATOR FOR BIOLOGICAL TISSUE UTILIZING OUTPUT CURRENT MONITOR

BACKGROUND OF THE INVENTION

The present invention relates generally to electrical stimulators for biological tissue and more particularly to an electrical current output circuit for an electrical stimulator for biological tissue.

Electrical stimulators providing an electrical stimulus signal are useful exciting for biological tissue. One significant use for electrical stimulators of this type is for transcutaneous electrical nerve stimulation (TENS) in which carefully controlled electrical stimulus signals are generated and then delivered via suitable electrodes through a patient's skin to underlying biological tissue. The electrical stimulus signals can be utilized for the purpose of masking neurally conducted pain signals; for example, the sensation of pain felt by a patient after surgery. Because of a patient's response to transcutaneous electrical nerve stimulation may vary significantly, a wide range of electrical stimulus parameters must be provided. A second use of electrical stimulators is for neuromuscular stimulation (NMS) in order to initiate or control muscular action in a patient. Since a wide variety of muscular actions are available, a wide variety of electrical stimulus signals must again be provided.

Electrical stimulators of biological tissue are typically attached to the biological tissue with electrodes. It is generally desirable that the electrode-tissue interface be low in impedance. If the impedance of the electrode-tissue interface is low, then most of the power supplied by the electrical stimulator will reach the biological tissue. However, the electrode-tissue interface sometimes exhibits a high impedance. If the electrode-tissue interface develops a high impedance, then much of the power provided by the electrical stimulus signal will be dissipated at the electrode-tissue interface instead of in the intended biological tissue. Such power dissipation at the electrode-tissue interface may cause skin irritation and other deleterious side effects. Moreover, this condition may lead to insufficient stimulation of the biological tissue unless extremely high voltages are provided by the electrical stimulator. For these reasons, some electrical stimulators for biological tissue utilize an impedance monitoring system to attempt to detect the condition of a high electrode-tissue interface impedance.

Prior art circuits have been utilized to sense for a high electrode-tissue impedance.

With a transformer driven output, one typical circuit has been constructed which utilizes an extra winding on the primary side of the output transformer output. If there is an extremely high load impedance across the secondary due to a poor electrode-tissue interface, the energy in the secondary will be reflected back to the primary winding and to the additional winding inserted on the primary side for this purpose and the energy in that winding is sensed. This solution adds to the cost, complexity and, size of the electrical stimulator due to the need for the additional transformer winding. Moreover, it is difficult to design an associated electronic circuit which will signal that a specific value of load impedance has been exceeded over a wide range of stimulus parameters and waveform types.

Another prior art circuit uses a series impedance element with the intended load. If there is little or no voltage across the series impedance element then the circuit knows that little or no current is flowing to the load and thus a high electrode-tissue interface impedance can be sensed. This circuit, however, is sensitive to ordinary variations and output current levels. In addition, sometimes the series impedance element is somewhat non-linear, i.e. may act as a rectifier. In this case, the series impedance element causes a DC shift in the electrical stimulus signal, resulting in polarization and possible deplating of the electrodes and in the occurrence of skin irritation.

SUMMARY OF THE INVENTION

The present invention provides a biological stimulator having a drive circuit for supplying an electrical stimulus signal used to stimulate biological tissue. Associated electrodes are designed to be capable of passing the electrical stimulus signal to associated biological tissue. The stimulator has a design impedance at which the stimulator may optimally operate, namely the electrode impedances, any electrode-tissue interface impedances and the associated biological tissue impedance. A transformer is provided having a primary winding and a secondary winding, the primary winding being operatively coupled to the drive circuit and the secondary winding being operatively coupled to the electrodes. A reference impedance having a value substantially greater than the value of the design impedance is coupled in parallel with the electrodes and, hence, the load. A current monitor for detecting the flow of current through the reference impedance, above a predetermined threshhold value, is coupled in series with the reference impedance and in parallel with the electrode and, hence, the load.

In a preferred embodiment of the present invention, a biological tissue stimulator is provided having a drive circuit for supplying an electrical stimulus signal used to stimulate biological tissue. Associated electrodes are designed which is capable of passing the electrical stimulus signal to associated biological tissue. The stimulator has a design impedance, namely the sum of electrode impedance(s), any biological tissue impedance, at which the stimulator may optimally operate. A transformer is provided having a primary winding and a secondary winding, the primary winding being operatively coupled to the drive circuit and the secondary winding being operatively coupled to the electrode. A reference impedance, having a value substantially greater than the value of the design impedance, is coupled in parallel with the load. A first current monitor is operatively coupled to the drive circuit for measuring the amount of current supplied by the drive circuit through the secondary winding of the transformer. A second current monitor for measuring the amount of current flowing through the reference impedance is coupled in series with the reference impedance and in parallel with the load. A comparator is operatively coupled to the first current monitor and to the second current monitor. The comparator is for comparing the current flow associated with the first and second current monitors and for determining if a predetermined difference in current flow is exceeded.

In another embodiment of the present invention, an electrical current output circuit for use in a biological tissue stimulator is adapted to a drive a load having a design impedance, namely the sum of electrode impedance(s), any electrode-tissue interface impedances and the associated biological tissue impedance. The electrical current output circuit has a drive circuit and a transformer having a primary winding and a secondary winding. The primary winding of the transformer is operatively coupled to the drive circuit and the secondary winding of the transformer being adapted to be coupled to the electrode. A reference impedance, having a value substantially greater than the value of the design impedance, is coupled in parallel with the load. A current monitor for detecting the flow of current through the reference impedance above a predetermined threshhold is coupled in series with the reference impedance and in parallel with the secondary winding and the load.

In an alternative embodiment of the present invention, an electrical current output circuit is provided for use in a biological tissue stimulator which is adapted to drive a load having a design impedance, namely, electrode impedance(s), any electrode-tissue interface impedances and the associated biological tissue impedance. The electrical current output circuit has a drive circuit and a transformer having a primary winding and a secondary winding. The primary winding of the transformer is operatively coupled to the drive circuit and the secondary winding of the transformer is adapted to be coupled to the electrode. A reference impedance, having a value substantially greater than the value of the design impedance, is coupled in parallel with the electrode and with the secondary winding of the transformer. A first current monitor is operatively coupled to the drive circuit for measuring the amount of current supplied by the drive circuit through the secondary winding of the transformer. A second current monitor for measuring the amount of current flowing through the reference impedance is coupled in series with the reference impedance and in parallel with the electrode and with the secondary winding of the transformer. A comparator is operatively coupled to the first current monitor and the second current monitor. The comparator compares the current flow associated with each of the first and second current monitors and determines if a predetermined difference in current flow is exceeded.

Thus, the electrical stimulator and output circuits of the present invention provide a significant advance over prior art circuits. The electrical stimulators and output circuits of the present invention utilize a comparision occurring through a reference impedance element which is in parallel with the load impedance. Since very little load current normally flows through the reference impedance, very little output power is normally dissipated in the reference impedance. The present invention does not utilize an additional winding on the primary of the transformer, thus, the transformer contained in the electrical stimulator of the present invention can be kept small in size. This is very important because the transformer size is very often the limiting size element in an electrical stimulator. Also, the electrical stimulators and output circuits of the present invention place no non-linear component in series with the load. Thus, the stimulators and circuits of the present invention do not lead to DC shift resulting in polarization of the electrodes. The reference impedance, being matched to the load sensed, provides a relative insensitivity to the stimulus waveform. Further, for those embodiments of the present invention which utilize the comparision of two current monitors, the comparison can be made over the entire output range of the electrical stimulator and the output circuits. The compared currents can be compared with the expected current, thus, maintaining the ability to have a constant reference impedance level over a wide range of output currents.

BRIEF DESCRIPTION OF THE DRAWINGS

The foregoing advantages, construction and operation of the present invention will become more readily apparent from the following description of the accompanying drawings in which.

DETAILED DESCRIPTION OF THE PREFERRED EMBODIMENTS

Figure 1:
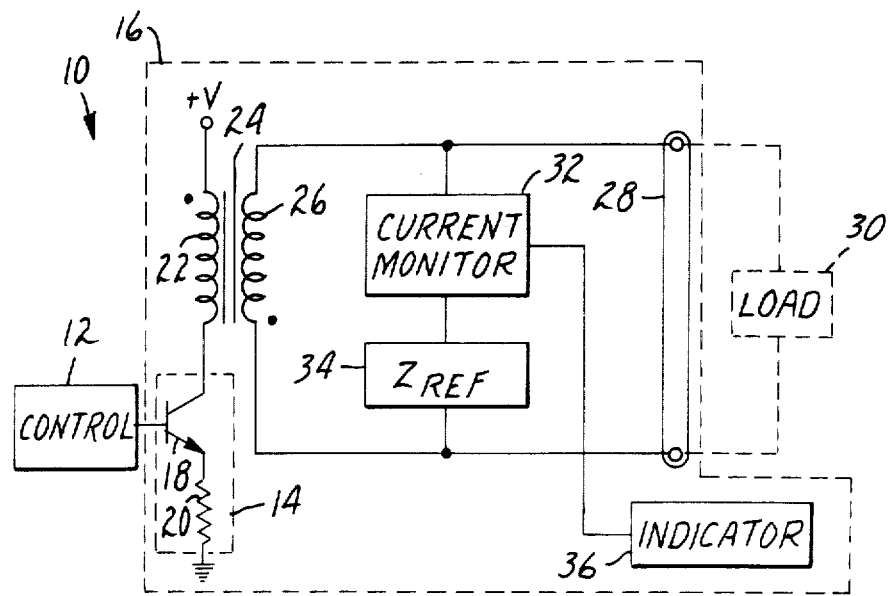
FIG. 1 is a block diagram representation of one embodiment of the present invention.

A block diagram of an electrical stimulator 10 is illustrated in FIG. 1. The electrical stimulator consists of a control portion 12 which selects and supplies an electrical stimulus signal to be used to stimulate biological tissue. Control portion 12 is of conventional design and may be easily formulated and specified by one of ordinary skill in the art. An example of a circuit which could be utilized for the control portion 12 is the control portion of a Myocare Plus TM electrical stimulator model no. 6810 manufactured by Minnesota Mining and Manufacturing Company, St. Paul, Minn. Control portion 12 supplies control signals for an electrical stimulus signal to drive circuit 14 of output circuit 16. Drive circuit 14 in FIG. 1 is represented by transistor 18 and emitter resistor 20. Drive circuit 14 is coupled via the collector of transistor 18 to the primary winding 22 of transformer 24. The secondary winding 26 of transformer 24 is coupled to an electrode system (consisting of two or more separate electrode elements, hereinafter simply referred to as "electrode") 28 which in turn is adapted to be coupled to a load 30 which is the biological tissue to be stimulated. Coupled in series with each other are a current monitor 32 and a reference impedance 34. Current monitor 32 and reference impedance 34 together are coupled in parallel with electrode 28 and, hence, in parallel with the load 30. The output of current monitor 32 is, optionally, coupled to indicator 36.

All of the current supplied by the secondary winding 26 of transformer 24 either passes through current monitor 32 or through load 30 via electrode 28. Reference impedance 34, connected in series with current monitor 32, serves to minimize the amount of curent from the secondary winding 26 which is diverted from the load 30 in order to monitor the current which is supplied by secondary winding 26. Thus, reference impedance 34 should be substantially greater than the expected value of the load impedance consisting of the sum of the impedance of electrode 28, any electrode-tissue (electrode-load) interface impedance, and the associated biological tissue (load) impedance. It is generally preferred that reference impedance 34 be at least 50 times the value of the expected load impedance. It has been found that in practice some electrical stimulators 10 operate in an environment with an expected load impedance of up to 2.5 kilohms and it has been found that the value of a reference impedance of at least about 25 kilohms is preferred.

Figure 2:
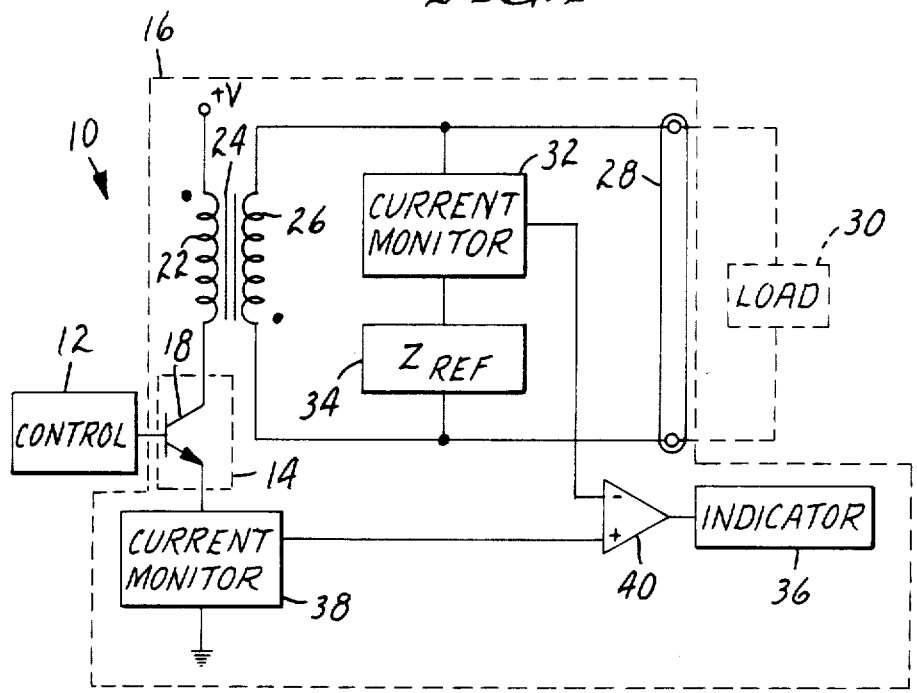
FIG. 2 is a block diagram of an alternative embodiment of the present invention.

FIG. 2 shows an alternative embodiment of the present invention. Again, electrical stimulator 10 consists of control portion 12 of conventional design similar to the design described with respect to FIG. 1. Control portion 12 drives output circuit 16, and particularly drive circuit 14. Drive circuit 14 consists of transistor 18 which is connected to the primary winding 22 of transformer 24. Secondary winding 26 of transformer 24 is connected to electrode 28 which in turn is adapted to be connected to load 30. Again, as in FIG. 1, current monitor 32 is coupled in series with reference impedance 34 and together are coupled in parallel with electrode 28 and, hence, adapted to be connected in parallel with load 30. A second current monitor 38 is coupled to drive circuit 14 for measuring the current supplied by drive circuit 14 to the primary winding 22 of transformer 24. The output of current monitor 32 and current monitor 38 is coupled to a comparator 40 which is used to measure the difference between the currents measured by current monitor 32 and current monitor 38. The result of such a difference, above a predetermined threshhold, can be supplied optionally to indicator 36.

Current monitor 38 provides an estimate of the current which should flow through current monitor 32 based upon the known turns ratio of transformer 24, the measured current through the primary winding 22 as measured by current monitor 38 and the ratio of the desired electrode-load impedance divided by the sum of the desired electrode-load impedance and reference impedance 34. If current monitor 32 provides the measurement of current which is significantly greater than this estimate, comparator 40 will change state to indicate that the electrode-load impedance has exceeded its desired values. Optionally, this trigger can be supplied to indicator 36 to visually or audibly indicate an alarm and/or to disable output circuit 16 of electrical stimulator 10.

Figure 3:
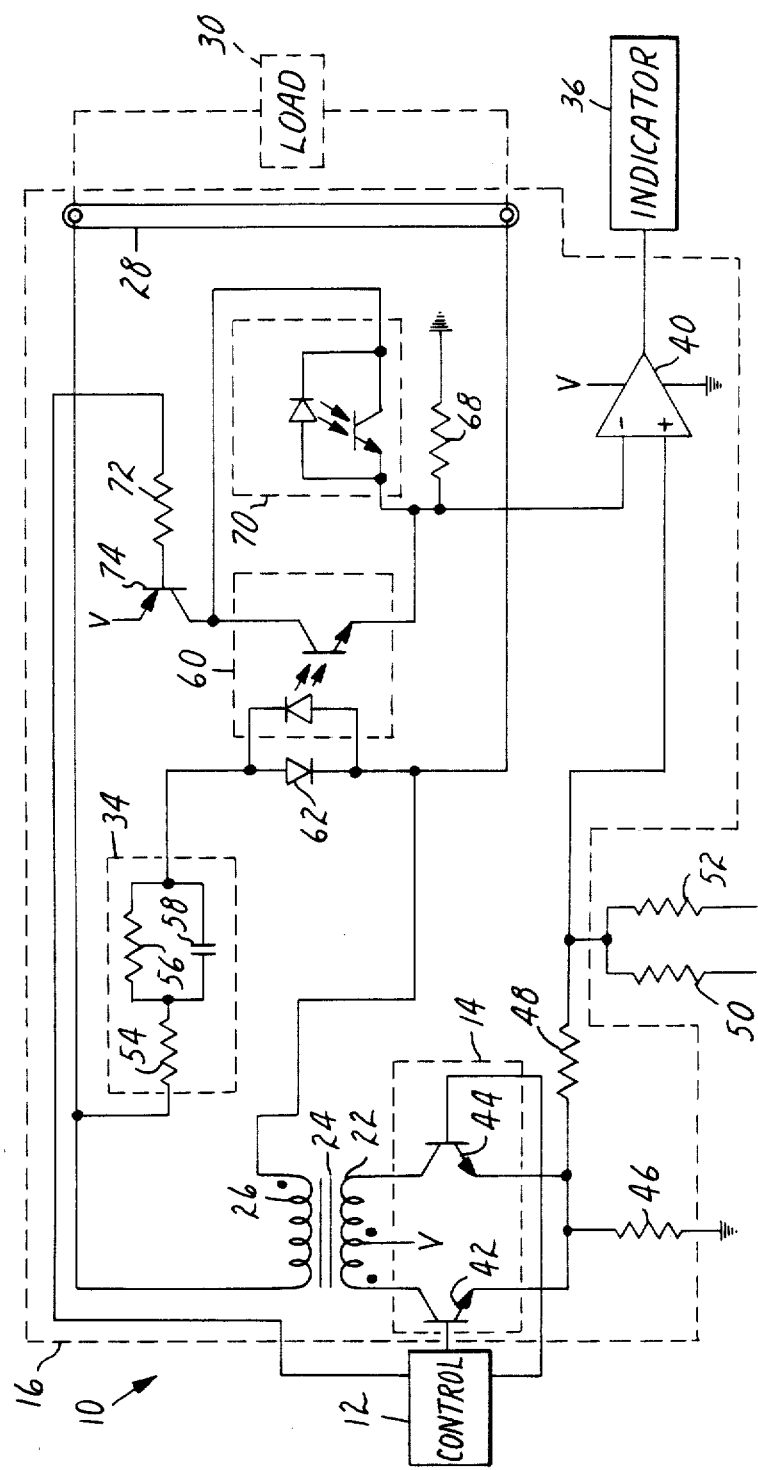
FIG. 3 is a schematic diagram of an alternative embodiment of the present invention also illustrating plural sensors.

A schematic diagram of a preferred embodiment is illustrated in FIG. 3. Again, electrical stimulator 10 comprises a control portion 12 of conventional design. Contained within output circuit 16 is drive circuit 16 is drive circuit 14 consisting of transistors 42 and 44 which provide push-pull drive of tne primary winding 22 of transformer 24. Transistors 42 and 44 provide a primary current proportional to the voltage appearing across reference resistor 46, forming one sensor, which in this embodiment operates as current monitor 38 of FIG. 2. Resistor 48 provides isolation between resistor 46 and comparator 40. Resistors 50 and 52 provide isolation for additional output stages which may share a common comparator 40. Reference impedance 34, forming another sensor, is formed by resistors 54, 56 and capacitor 58. The overall impedance of reference impedance 34 is chosen such that it is much greater than the desired electrode-load impedance. The current flowing through reference impedance 34 is, therefore, only a fraction of the current supplied to load 30. Reference impedance 34 is coupled through opto-isolator 60, and diode 62 which in this embodiment also serve as current monitor 32. Reference impedance 34 and opto-isolator 60 are coupled in series with each other and in parallel with electrode 28. Resistor 68 serves to set the threshhold value for the output from opto-isolator 60 to comparator 40. Further, opto-isolator 70 is illustrative that, in conjunction with resistors 50 and 52, devices such as opto-isolator 70 may be coupled to additional output circuits (not shown). Resistor 72 and transistor 74 serve as a gate to enable or disable opto-isolators 60 and 70. As in FIG. 2, comparator 40 may be optionally connected to an indicator alarm or output disabling means, (not shown).

A preferred embodiment of the components illustrated in FIGS. 1, 2 and 3 are given in table one as follows:

| Reference No. | Value or Type No. | Manufacturer |
| --- | --- | --- |
| 18 | ZTX-650 | Feranti |
| 20 | 0.24 ohms | |
| 24 | PRIMARY:SECONDARY = 32:640 | Precision |
| 40 | LM339 | Signetics |
| 42 | ZTX-650 | Feranti |
| 44 | ZTX-650 | Feranti |
| 46 | 0.24 ohms | |
| 48 | 1 kilohm | |
| 50 | 1 kilohm | |
| 52 | 1 kilohm | |
| 54 | 27 kilohms | |
| 56 | 150 kilohms | |
| 58 | 0.0022 microfarads | |
| 60 | HCPL-2531 | Hewlet Packard |
| 62 | IN4148 | |
| 68 | 68 ohms | |
| 70 | HCPL-2531 | Hewlet Packard |
| 72 | 22 kilohms | |
| 74 | 2N3906 | |

Thus, it can be seen that there has been shown and described a novel electrical stimulator for biological tissue utilizing an output current monitor. It is to be understood, however, that various changes, modifications and substitutions in the form or the details of the described invention can be made by those skilled in the art without departing from the scope of the invention as defined by the following claims.

What is claimed is:

1. A biological tissue stimulator, comprising:

control means for selecting and supplying electrical stimulus parameters;

drive circuit means coupled to said control means for supplying an electrical stimulus signal from said electrical stimulus parameters and adapted to stimulate biological tissue;

an electrode designed to be capable of passing said electrical signal to associated biological tissue;

said stimulator may optimally operate comprising said electrode, associated biological tissue and any electrode-tissue interfaces;

a transformer having a primary winding and a secondary winding, said primary winding being operatively coupled to said drive circuit means; said secondary winding being operatively coupled to said electrode;

a reference impedance having a value of at least 10 times the value of said design impedance;

a current monitor for detecting the flow of current through said reference impedance above a predetermined threshold value;

said reference impedance and said current monitor being coupled in series with each other and in parallel with said secondary winding and said electrode; and indicator means responsive to said current monitor for indicating if said predetermined threshold has been exceeded.

2. A biological stimulator as in claim 1 in which said reference impedance has a value of at least 50 times the value of said design impedance.

3. A biological tissue stimulator as in claim 1 in which said reference impedance has a value of at east 2.5 kilohms.

4. A biological tissue stimulator, comprising:
control means for selecting and supplying electrical stimulus parameters;
drive circuit means coupled to said control means for supplying an electrical stimulus signal from said electrical stimulus parameters and adapted to stimulate biological tissue;
an electrode designed to be capable of passing said electrical signal to associated biological tissue;
said stimulator having a design impedance at which said stimulator may optimally operate comprising said electrode, associated biological tissue and any electrode-tissue interface;
a transformer having a primary winding and a secondary winding, said primary winding being operatively coupled to drive circiut, said secondary winding being operatively coupled to said electrode;
a reference impedance having a value of at least 10 times the value of said design impedance;
a first current monitor operatively coupled to said drive circuit means for measuring the amount of current supplied by said drive circuit to said primary winding of said transformer;
a second current monitor for measuring the amount of current flowing through said reference impedance;
said reference impedance and said second current monitor being coupled in series with each other and in parallel with said secondary winding of said transformer;
a comparator being operatively coupled to said first current monitor and to said second current monitor; said comparator for comparing the current flow associated with said first and second current monitors and for determining if a predetermined difference in current flows is exceeded;
indicator means responsive to said current monitor for indicating if said predetermined threshold has been exceeded.
whereby it can be determine if the flow of current through said reference impedance exceeds a predetermined fraction of the total current flow delivered by said drive circuit means through said secondary winding indicative of said load having an excessively high impedance value such as is caused by poor electrical contact between said electrode and said biological tissue.

5. A biological tissue stimulator as in claim 4 in which said reference impedance has a value of at least 50 times the value of said design impedance.

6. A biological tissue stimulator as in claim 4 in which said reference impedance has a value of at least 2.5 kilohms.

* * * * *

UNITED STATES PATENT AND TRADEMARK OFFICE
CERTIFICATE OF CORRECTION

PATENT NO. : 4,706,674

DATED : November 17, 1987

INVENTOR(S) : Alan P. Dieken and Joel R. Dufresne

It is certified that error appears in the above-identified patent and that said Letters Patent is hereby corrected as shown below:

Col. 2, line 41, after "any" insert --electrode-tissue interface impedances and the associated--.

Col. 5, line 42, "is drive circuit 16" should be deleted.

Col. 5, line 44, "tne" should read --the--.

Col. 6, line 49, after "stimulator" insert --having a design impedance at which said stimulator--.

Col. 7, line 5, "east" should read --least--.

Signed and Sealed this

Fourteenth Day of June, 1988

Attest:

DONALD J. QUIGG

*Attesting Officer*

*Commissioner of Patents and Trademarks*